United States Patent [19]
Farren

[11] Patent Number: 5,863,506
[45] Date of Patent: Jan. 26, 1999

[54] AUTOMATIC CHEMISTRY ANALYZER WITH IMPROVED HEATED REACTION CUP ASSEMBLY

[75] Inventor: Carl A. Farren, Placentia, Calif.

[73] Assignee: Beckman Instruments, Inc., Fullerton, Calif.

[21] Appl. No.: 746,313

[22] Filed: Nov. 12, 1996

[51] Int. Cl.⁶ .................................................. G01N 21/03
[52] U.S. Cl. .............................. 422/102; 422/63; 422/64; 422/104; 436/43; 436/49; 436/165; 436/180
[58] Field of Search ............................... 422/63, 67, 68.1, 422/81, 82.03, 82.05, 100, 102, 103, 104; 436/43, 49, 164, 165, 174, 179, 180; 392/465, 467; 219/521

[56] References Cited

U.S. PATENT DOCUMENTS

| | | | |
|---|---|---|---|
| 3,964,867 | 6/1976 | Berry | 422/64 |
| 4,086,061 | 4/1978 | Hoffa et al. | |
| 4,200,607 | 4/1980 | Suzuki | 422/64 |
| 4,367,198 | 1/1983 | Scordato et al. | 422/102 |
| 4,443,407 | 4/1984 | Weinberg et al. | 422/68 |
| 4,689,862 | 9/1987 | Kitagawa et al. | 219/200 |
| 4,727,032 | 2/1988 | Baisch et al. | 436/47 |
| 4,788,150 | 11/1988 | Nelson et al. | 436/45 |
| 4,858,155 | 8/1989 | Okawa et al. | 364/557 |
| 4,889,691 | 12/1989 | Argentieri | 422/102 |
| 4,965,049 | 10/1990 | Lillig et al. | |
| 5,089,230 | 2/1992 | Kondo et al. | 422/64 |
| 5,133,937 | 7/1992 | Frackleton et al. | 422/81 |
| 5,162,236 | 11/1992 | Pang et al. | |
| 5,241,415 | 8/1993 | Argentieri | 359/395 |
| 5,314,825 | 5/1994 | Weyrauch et al. | 436/43 |
| 5,410,130 | 4/1995 | Braunstein | 219/521 |

FOREIGN PATENT DOCUMENTS

| | | |
|---|---|---|
| 0 408 182 A2 | 1/1991 | European Pat. Off. |
| WO92/10294 | 6/1992 | WIPO |

OTHER PUBLICATIONS

"An Automatic Method For Colorimetric Analysis," Leonard T. Skeggs, Jr., Ph.D., American Journal of Clinical Pathology, vol. 28, pp. 311–322, 1957.

Primary Examiner—Long V. Le
Attorney, Agent, or Firm—William H. May; Margaret A. Kivinski; Sheldon & Mak

[57] ABSTRACT

The invention provides an automatic analyzing machine comprising a unique reaction cup combination for running high volume chemical analyses, such as analyses for sodium, potassium, glucose, creatinine and BUN (blood urea nitrogen). The reaction cup combination includes an aluminum body having at least one flat smooth side. A planar heating element is sandwiched between the flat side and a planar outer sidewall. Within the planar outer sidewall is disposed a reagent inlet conduit coiled or otherwise disposed in planar fashion. By this design, heating of inlet reagent is more efficient and control of the temperature within the reaction cup is more precise. In a preferred embodiment, the reaction cup assembly includes a pair of such heating element and inlet conduit combinations so that the reaction cup can be rinsed with heated water instead of heated reagent. Such a design not only reduces the use of expensive reagent, but minimizes toxic waste disposal needs.

16 Claims, 13 Drawing Sheets

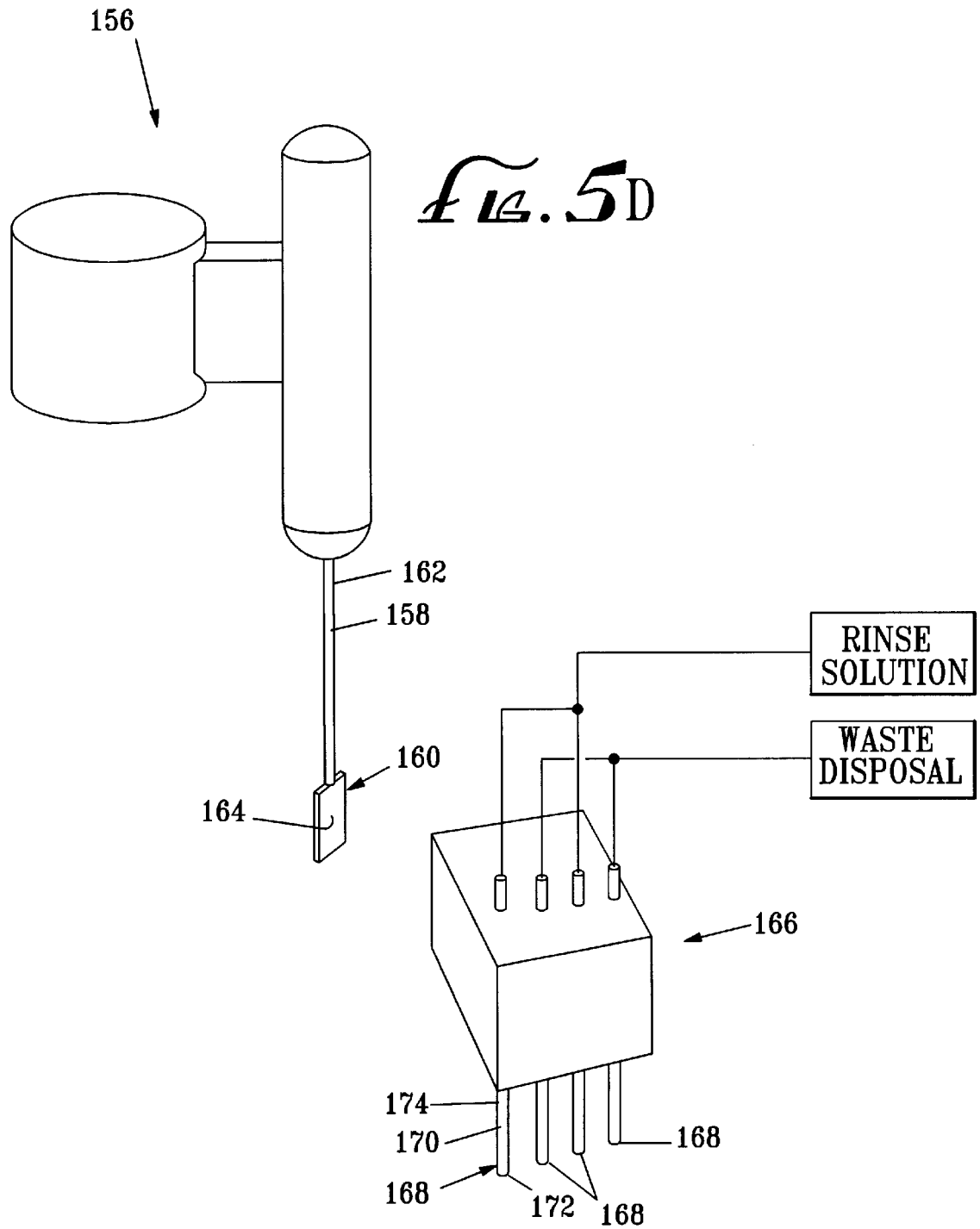

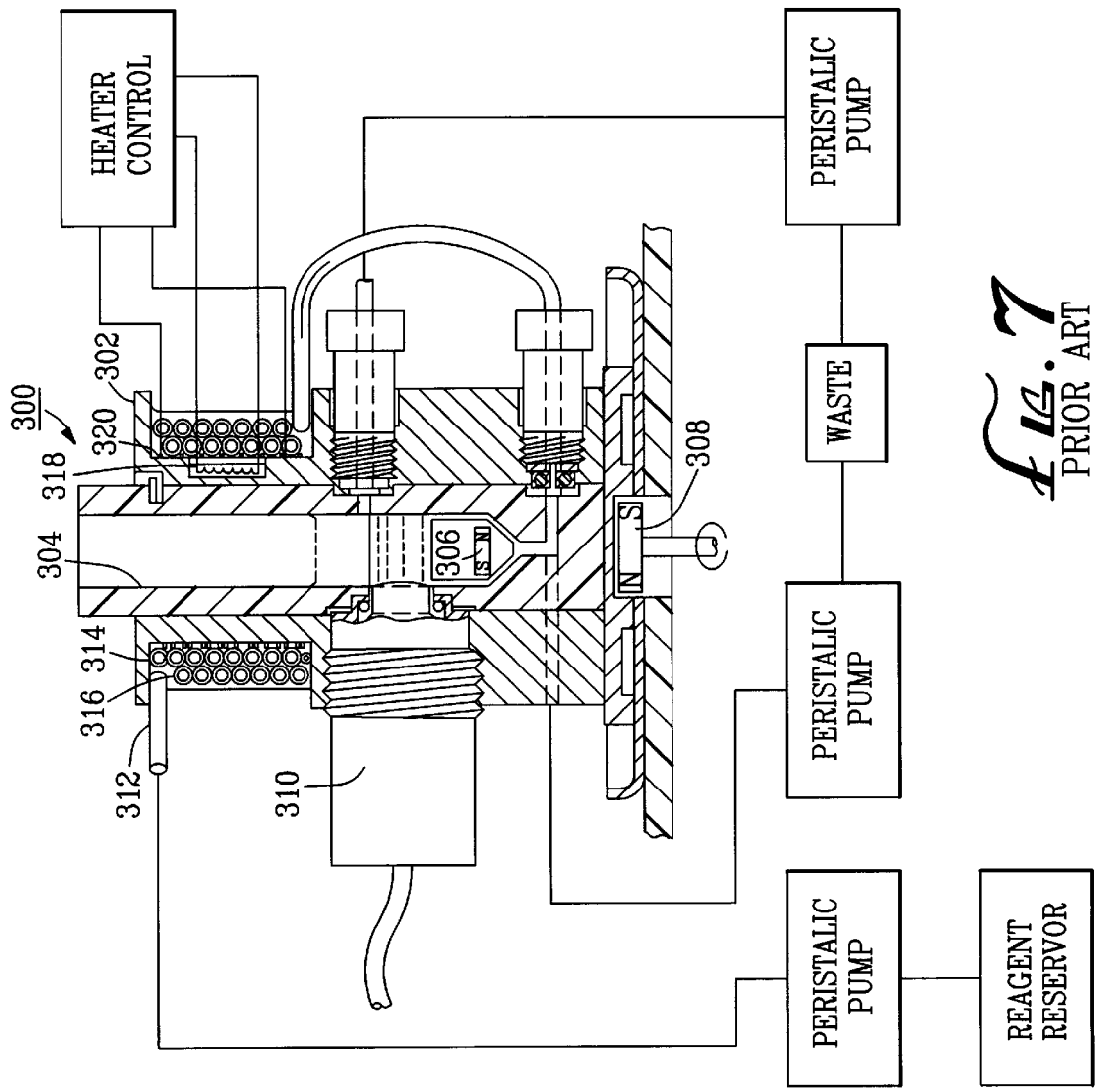

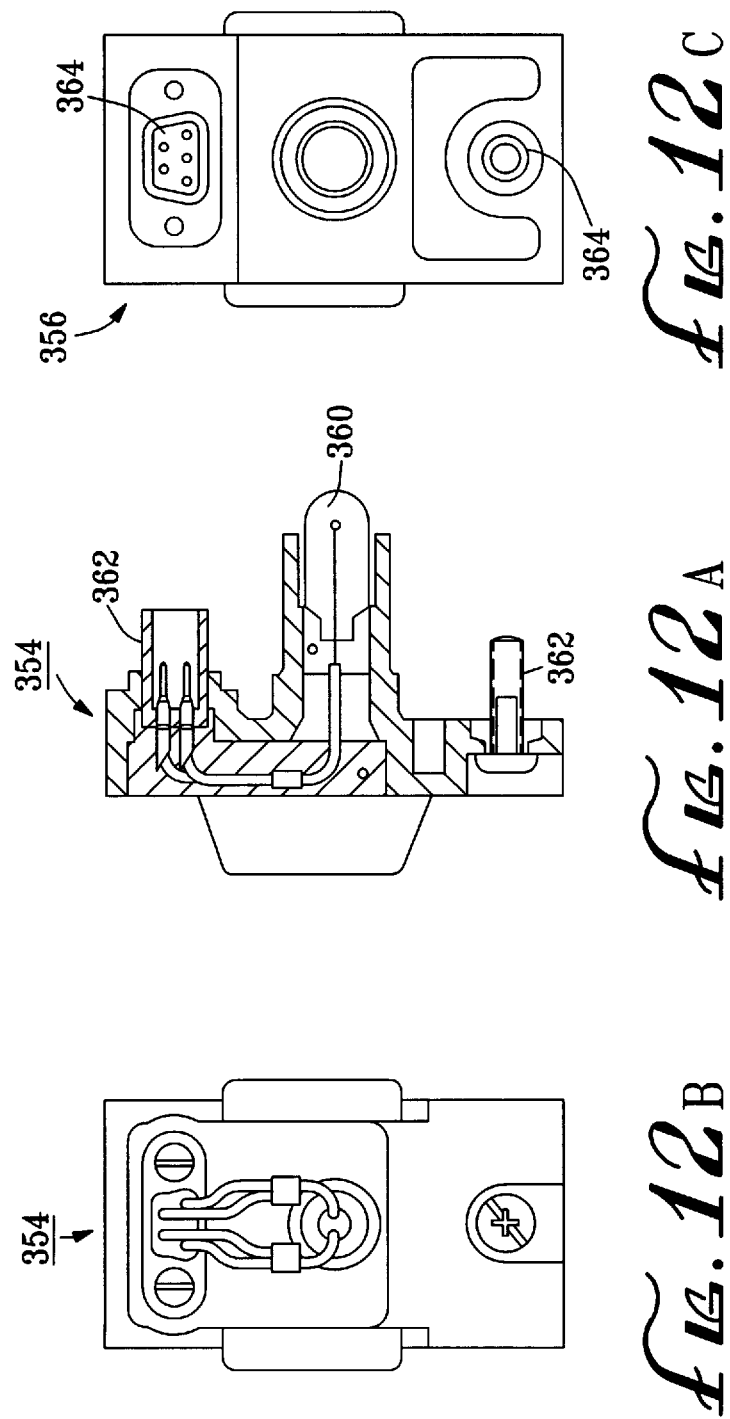

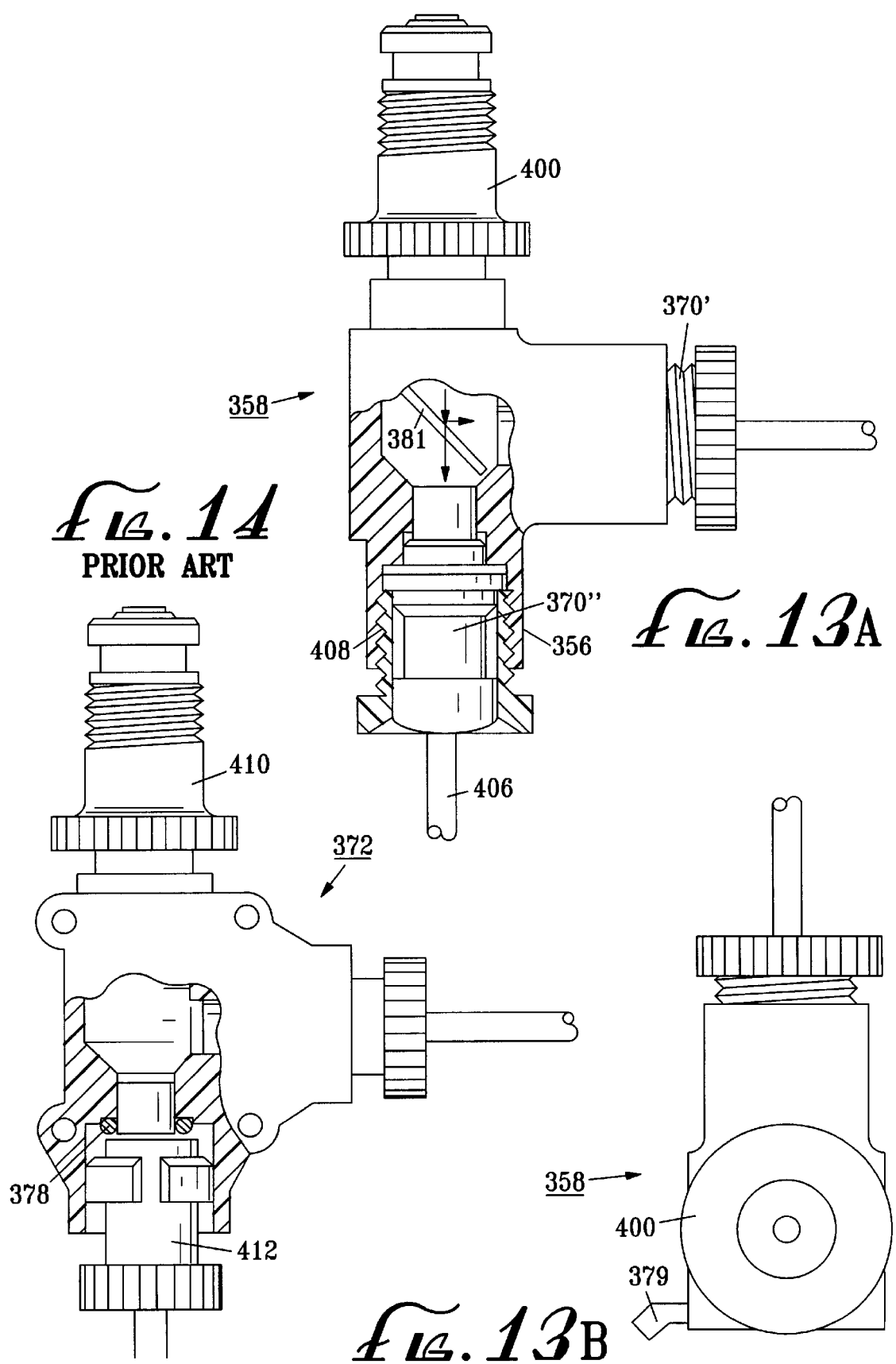

AUTOMATIC CHEMISTRY ANALYZER WITH IMPROVED HEATED REACTION CUP ASSEMBLY

FIELD OF THE INVENTION

This invention generally relates to the field of automated clinical chemical analyzers, and specifically to high throughput automated chemical analyzers having high volume, limited menu analyzer modules.

BACKGROUND OF THE INVENTION

A number of different automated clinical chemical analyzers are known in the art. Such analyzers range from simple, largely manually-operated instruments to highly complex, nearly fully automated instruments. Each analyzer has its own particular performance characteristics related to the number of different tests ("menu") that the analyzer can perform and the number of samples that can be processed in a given period of time ("throughput").

Large scale, highly complex analyzers useful in large hospitals and clinical laboratories have been developed which have both a large menu of tests which the instrument can perform and a high throughput. Such an analyzer is described in U.S. Pat. No. 4,965,049 issued to Lillig et al. which is incorporated herein by reference in its entirety.

In U.S. Pat. No. 4,965,049, it is recognized that the throughput of a large menu analyzer can be increased by performing frequently requested analyses in high volume, limited menu analyzer modules separate from broader menu analyzer modules. Such high volume, limited menu modules are commonly used for such frequently requested analyses as sodium, potassium, glucose, creatinine and blood urea nitrogen ("BUN").

As sophisticated and efficient as many of today's large scale analyzers are, several problems continue to exist. First and foremost is throughput capacity. Every second which can be saved in the analysis time of each sample means millions of dollars in savings of precious medical resources. Therefore, there is continuous pressure on analyzer manufactures to increase throughput. In prior art high volume, limited menu modules, the required rinsing step between each analysis is carried out using the same reagent which is employed in the analysis. This results in a loss of module turnaround because the rinsing reagent must either be preheated (to maintain the temperature of the module) or (if non-preheated reagent is used) the module must be reheated after rinsing prior to its being used in another chemistry.

Also, in analyzing machines using nephelometry to analyze the results of the chemistry carried out within the module, throughput is reduced by having to periodically calibrate the nephelometer.

An additional problem is maintenance. Users of large scale analyzers require an extremely high standard of reliability. In high volume, limited menu analyzer modules which use nephelometry, several problems related to reliability exist in the prior art. Typically, the nephelometric analyzer uses a light source, a focusing lens, a receiving lens and a light receptor. In prior art nephelometric analyzer manufacturing processes, the forward end of the light source is, itself, shaped like a lens. However, the quality of such lens shaping varies from light source to light source. Thus, with every analyzer, the light energy emanating from the focusing "lens" varies depending upon the relative quality of alignment. In the prior art, the analyzing machine manufacturer had to compensate for these alignment problems by calibrating each analyzer after it was installed in the analyzing machine using modulating shutters disposed between the focusing "lens" and the reaction cup. Use of such shutters requires that the light source be operated at near maximum capacity. Thus, prior art light sources tend to burn out quickly. Also, a problem arises at the time that the light source burns out and needs to be replaced. The analyzer shutters have to be recalibrated anew. Since the recalibration operation is complex and requires considerable skill, the simple occurrence of a burned out light source bulb in the prior art causes a significant maintenance problem for the user.

Another problem with the prior art is reliability. In prior art light source modules, the light receptor housing is attached within the reaction cup using a bayonet connection. Minimum resistance to rotation in the bayonet connection is provided solely by the resilient pressing of the forward end of the receptor housing against a flexible O-ring. Unfortunately, this connection can easily be bumped out of alignment, such as by minor physical contact with the light receptor housing. Any such misalignment throws the analysis module out of calibration.

Still another problem with the prior art is that high volume, limited menu analyzer modules of the prior art are typically expensive to operate because they use a considerable amount of reagent (because the rinsing step mentioned above is carried out with expensive reagent) and because of excessive waste disposal costs (again, because potentially toxic reagent is often used as the rinsing agent).

Accordingly, there is a need for a high volume, limited menu analyzer module which has greater throughput than similar prior art analyzer modules, requires less maintenance, is more reliable and does not cost as much to operate.

SUMMARY OF THE INVENTION

The invention satisfies these needs. The invention is a reaction cup combination useful for automated chemical analyses comprising (a) a body having at least one substantially smooth flat side, (b) a reaction cup disposed within the body, (c) an analyzer for analyzing liquids disposed within the reaction cup, (d) a planar heating element disposed in abutment with the flat side of the body, (e) a planar side wall disposed proximate to the heating element, and (f) an inlet conduit disposed in fluid communication with the reaction cup. The inlet conduit is disposed substantially within the planar side wall so that the inlet conduit is in abutment with the heating element.

In a typical embodiment, the body has a first substantially flat side and a second substantially flat side and the reaction cup combination comprises (a) a first planar heating element disposed in abutment with the first flat side of the body, (b) a first planar side wall disposed proximate to the first heating element, (c) a first inlet conduit disposed in fluid communication with the reaction cup, the first inlet conduit being disposed substantially within the first planar side wall such that the first inlet conduit is in abutment with the first heating element, (d) a second planar heating element disposed in abutment with the second flat side of the body, (e) a second planar side wall disposed proximate to the second heating element, and (f) a second inlet conduit disposed in fluid communication with the reaction cup, the second inlet conduit being disposed substantially within the second planar side wall such that the second inlet conduit is in abutment with the second heating element.

Preferably, the reaction cup combination further comprises (a) a first drain conduit disposed in fluid communication with the reaction cup, (b) a second drain conduit disposed in fluid communication with the reaction cup, and (c) a drain valve controller for controlling the opening and closing of drain conduit valves in each of the drain conduits. Typically, one drain conduit is directed to non-hazardous waste disposal and the other drain is directed to a toxic waste disposal.

In one embodiment, the analyzer is a nephelometer. In such an embodiment, the reaction cup side walls have opposed first and second substantially transparent wall portions and the reaction cup combination further comprises (a) a light source housing disposed adjacent to the first transparent wall portion, the light source housing including a bulb housing moiety and a lens housing moiety, (b) a light receptor housing disposed adjacent to the second transparent wall portion, (c) a light receptor disposed within the light receptor housing, (d) a light bulb rigidly affixed within the bulb housing moiety so that light produced by the light bulb is directed into the lens housing moiety, and (e) a lens rigidly affixed within the lens housing moiety so that light produced by the light bulb is directed through the first and second transparent wall portions to the light receptor, the lens being separate and spaced apart from the light bulb.

Preferably, the light receptor housing is rigidly disposed adjacent the second transparent wall portion and the light receptor is rigidly disposed within the light receptor housing.

The invention is also an automated analyzing machine comprising the reaction cup assembly described above.

The invention is also a method of analyzing samples using the reaction cup assembly described above.

The invention provides significant improvements over the prior art by reducing maintenance costs and operating expense, while increasing throughput accuracy and reliability.

DESCRIPTION OF THE DRAWINGS

These and other features, aspects and advantages of the present invention will become better understood with reference to the following description, appended claims and accompanying drawings where:

FIG. 5D is a perspective view of a cuvette stirring rod assembly;

FIG. 5E is a perspective view of a cuvette wash station;

FIG. 7 is a cross-sectional view of a reaction cup module known in the prior art;

FIG. 12A is a cross-sectional side view of a light bulb subassembly useful in the light source housing shown in FIG. 12;

FIG. 12B is a first end view of a light source lens subassembly useful in the light source housing shown in FIG. 12;

FIG. 12C is a second end view of the light source lens subassembly useful in the light source housing shown in FIG. 12;

FIG. 13A is a cross-sectional side view of a light receptor housing having features of the invention;

FIG. 13B is a front side view of the light receptor housing shown in FIG. 14A; and FIG. 14 is a cross-sectional view of a light receptor housing known in the prior art.

DETAILED DESCRIPTION OF THE INVENTION

The following discussion describes in detail one embodiment of the invention and several variations of that embodiment. This discussion should not be construed, however, as limiting the invention to those particular embodiments. Practitioners skilled in the art will recognize numerous other embodiments as well. For a definition of the complete scope of the invention, the reader is directed to the appended claims.

Figure 1:
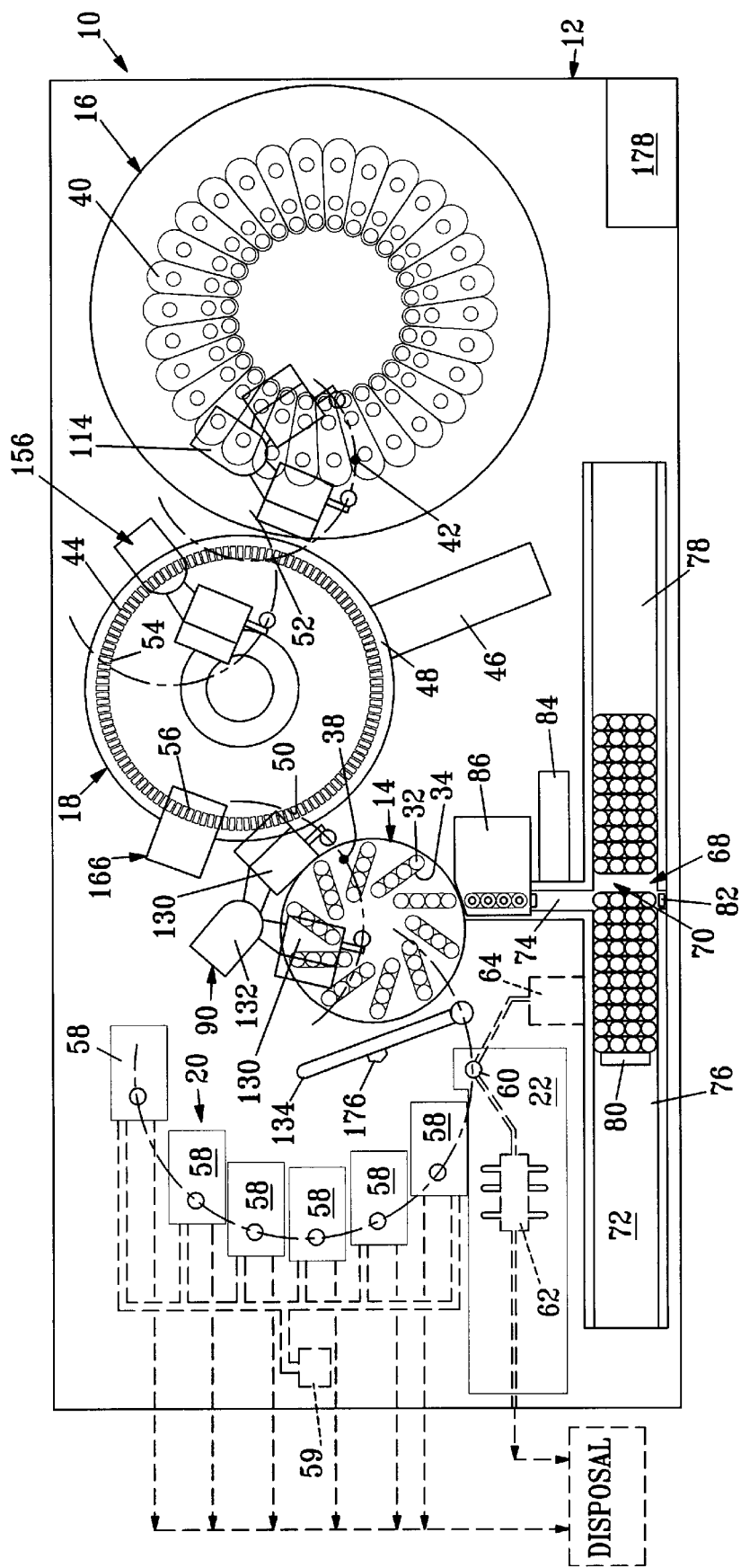
FIG. 1 is a schematic plan view of an automated analyzing machine having features of the invention.
Figure 2:
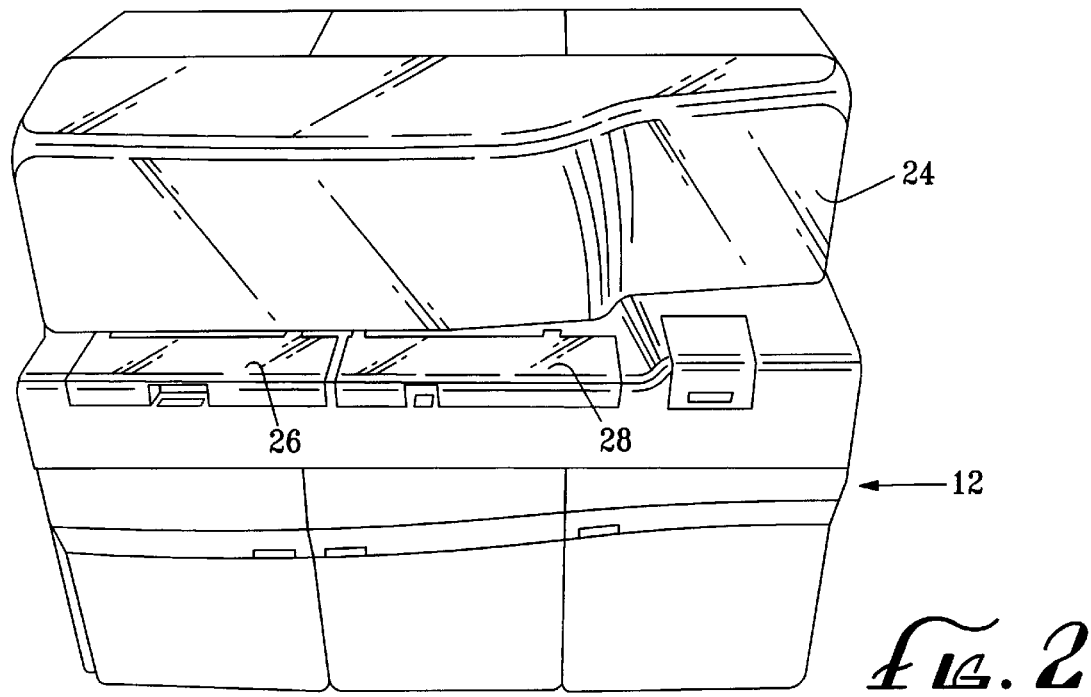
FIG. 2 is a front view of an automated analyzing machine having features of the invention with its canopy closed.
Figure 3:
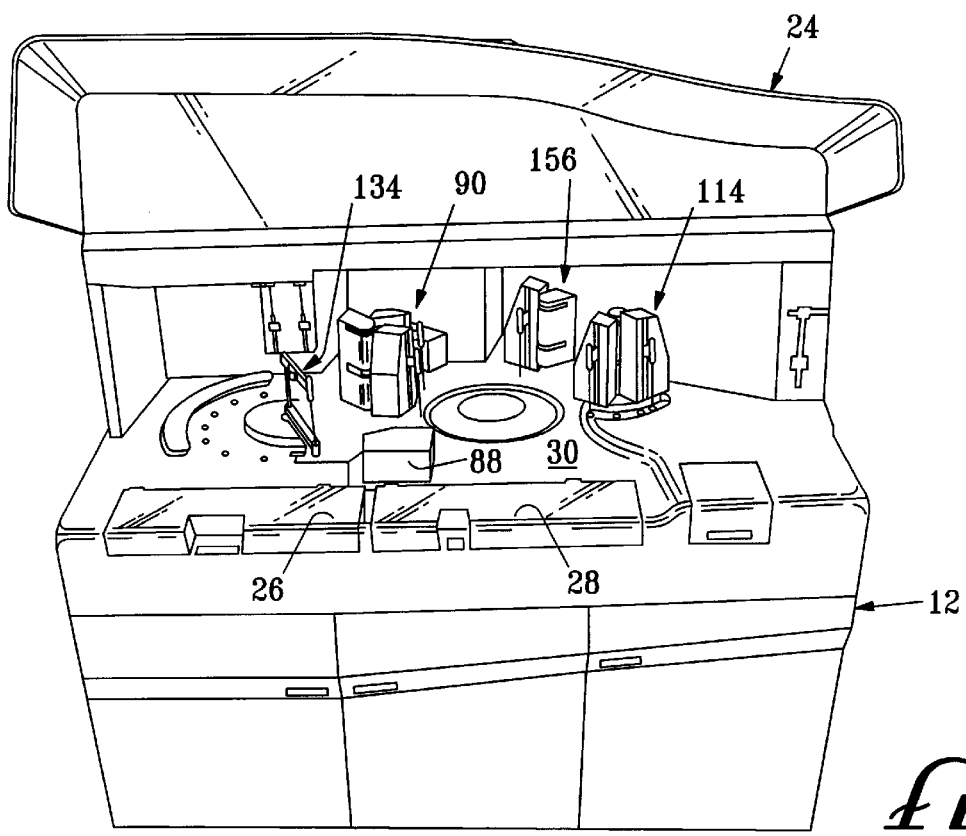
FIG. 3 is another front view of the automated analyzing machine of FIG. 2 shown with its canopy open.

FIGS. 1–3 show an automated analyzing machine 10 having features of the invention. The machine 10 comprises a body 12, a sample station 14, a reagent station 16, a random access analyzing station 18, a reaction cup analyzing station 20 and an ion selective electrode analyzing station 22.

The body 12 is typically a cabinet providing a housing for the various operative components. The body 12 is typically made from a lightweight metal such as a lightweight sheet steel. The embodiment shown in FIGS. 2 and 3 includes a hinged primary canopy 24. FIG. 2 shows the analyzing machine 10 with the primary canopy 24 closed. FIG. 2 shows the machine with the primary canopy 24 open.

FIGS. 2 and 3 also illustrate how a typical analyzing machine 10 of the invention can have an on-load tray cover 26, an off-load tray cover 28 and one or more operator area covers 30 covering the sample station 14, the reagent station 16, the random access analyzing station 18, the reaction cup analyzing station 20 and the ion selective electrode analyzing station 22.

Figure 4A:
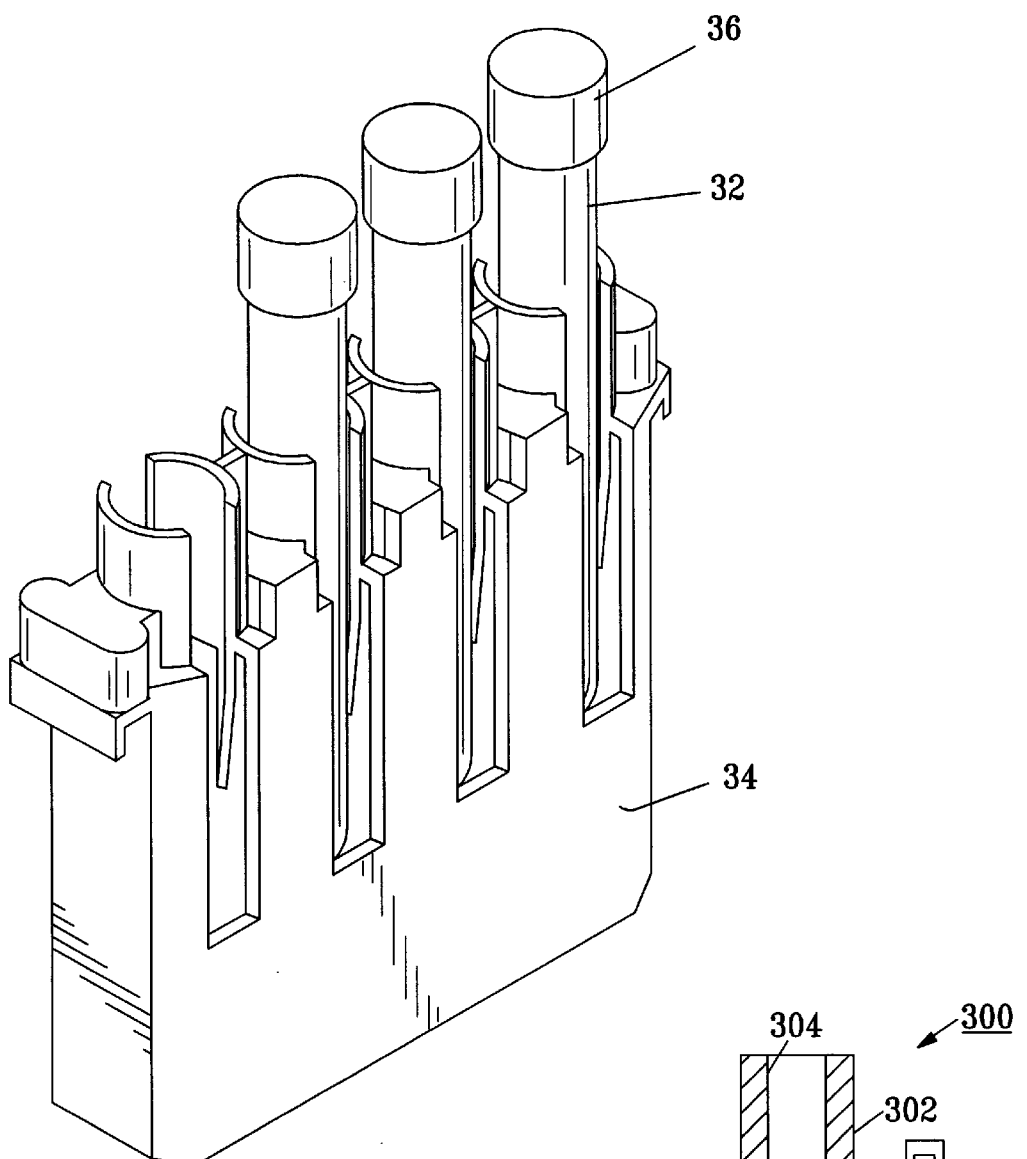
FIG. 4A is a perspective view of a sample container rack and sample containers useful in the invention.

The sample station 14 is sized and dimensioned to retain a plurality of sample containers 32. In the embodiment shown in FIGS. 1–3, the sample station 14 is a revolving circular carousel capable of retaining 40 sample containers 32 disposed in 10 sample container racks 34. In a typical embodiment, each sample container 32 is a generally upright container having a container cap 36 of thin rubber or like material. A sample container rack 34 containing four sample containers 32 useful in the invention is shown in FIG. 4A. The sample station 14 is moveable by a rotating motor (not shown) such that each sample container 32 can be alternatively positioned under and moved away from at least one sample extraction site 38.

The reagent station 16 is sized and dimensioned to retain a plurality of reagent containers 40. Each reagent container 40 contains one or more compartments for retaining one or more different reagents useful in the analysis chemistry performed by the analyzing machine 10. Also, it is preferable to predilute the reagent to minimize reagent usage and dilution step delays. A preferred reagent container 40 design has three individual compartments and is described in detail in U.S. Pat. Nos. 4,970,053 and 5,075,082, which are both incorporated herein by this reference in their entireties.

Preferably, the reagent station 16 is refrigerated, such as to a temperature of about 4° C., to preserve reagent life and minimize evaporation.

In the embodiment shown in FIGS. 1–3, the reagent station 16 is a revolving circular carousel. The reagent station 16 is movable by a rotating motor (not shown) such that each reagent container 40 can be alternatively positioned under and moved away from at least one reagent extraction site 42.

Preferably, the reagent station 16 also includes a bar code reader (not shown) which reads bar-coded information printed on the reagent containers 40 and/or disposed on the reagent carousel. Such information can be transmitted to a computerized controller to assist in operation of the analyzing machine 10.

Figure 4B:
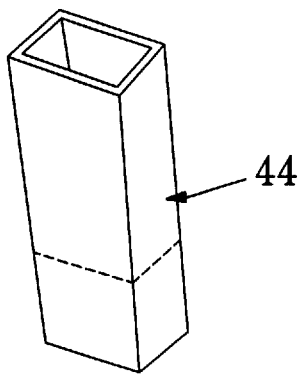
FIG. 4B is a perspective view of a reaction cuvette useful in the invention.
Figure 4C:
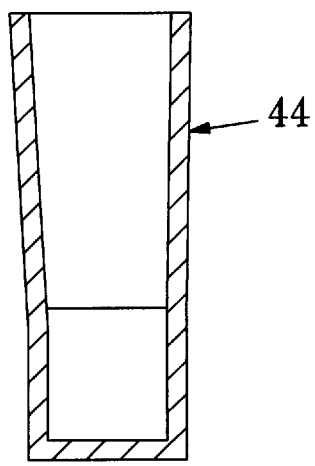
FIG. 4C is a cross-sectional side view of the reaction cuvette shown in FIG. 4B.

The random access analyzing station 18 is sized and dimensioned to retain a plurality of reaction cuvettes 44 as illustrated in FIGS. 4B and 4C. In the embodiment shown in FIGS. 1–3, the random access analyzing station 18 is a revolving circular carousel capable of retaining in excess of 100 cuvettes 44. Each cuvette 44 is a small open top reaction container having at least two opposed transparent sides through which a beam of light can be directed.

The random access analyzing station 18 further comprises random access analyzing station analyzer 46, such as a nephelometer and/or photometer disposed proximate to a random access analyzing station analyzing site 48 for determining at least one parameter of a sample disposed within the cuvettes 44.

The random access analyzing station 18 is movable by a rotating motor (not shown) such that each cuvette 44 can be alternatively positioned under and moved away from at least one cuvette sample deposit site 50, at least one cuvette reagent deposit site 52, at least one cuvette mixing site 54, at least one cuvette washing site 56 and the one random access analyzing station analyzing site 48.

The reaction cup analyzing station 20 comprises at least one reaction cup module 58. In the embodiment shown in FIG. 1, the reaction cup analyzing station 20 comprises six reaction cup modules 58. Each reaction cup module is in fluid communication with a source of suitable reagent which can be pumped in the module using one or more reagent pumps 59. In a typical operation, each reaction cup module 58 has its own pump 59. Each reaction cup module 58 is also in communication with one or more suitable disposal sites. The details of these reaction cup modules are explained in detail below.

The ion selective electrode analyzing station 22 comprises a sample injection cup 60 disposed in fluid tight communication with a flow cell analyzer 62 capable of measuring at least one electrolyte in a liquid sample. The sample injection cup 60 is also disposed in fluid tight communication with an ion selective electrode analyzing station pump 64 capable of pumping at least one ion selective electrode analyzing reagent from a source of such reagent (not shown) to the sample injection cup 60 and also capable of pumping the contents of the sample injection cup 60 through the flow cell analyzer 62 and then to a suitable disposal site.

In the embodiment shown in the drawings, the analyzing machine 10 further comprises a sample container loading and preparation assembly 68. The loading and preparation assembly 68 comprises a loading mechanism 70 for loading one or more sample containers from a loading area 72 to the sample station 14 along a loading mechanism path 74. The loading mechanism 70 comprises an on-load tray 76 and an off-load tray 78. In the embodiment shown in FIG. 1, the on-load tray 76 and the off-load tray 78 are sized and dimensioned to retain a plurality of sample container racks 34. The on-load tray 76 has a motorized loading arm 80 for pushing a plurality of sample container racks 34 towards the loading mechanism path 74. The off-load tray 78 has a motorized unloading arm (not shown) for pushing the sample container racks 34 away from the loading mechanism path 74.

The loading mechanism path 74 has a motorized loading path arm 82 which moves a single sample container rack 34 along the loading mechanism path 74 on to and off from the sample station 14. A bar code reader 84 is typically disposed along the loading mechanism path 74. The bar code reader 84 is capable of reading bar coded information disposed on each individual sample container 32 as the sample container 32 moves along the loading mechanism path 74.

In the embodiment shown in FIG. 1, the sample container loading and preparation assembly 68 further comprises a sample container cap piercing mechanism 86 capable of piercing the sample container caps 36 so as to leave the caps 36 open for access by the sample extraction cup analysis probes (described below).

As illustrated in FIGS. 2 and 3, the sample container cap piercing mechanism 86 can be disposed under a sample cap piercing mechanism cover 88.

A particularly useful sample cap piercing mechanism 86 is disclosed in detail in U.S. patent application Ser. No. 08/746,560, entitled AUTOMATIC CHEMISTRY ANALYZER WITH IMPROVED HEATED ION SELECTIVE (presently pending), filed contemporaneously herewith, and which is incorporated herein by reference in its entirety.

Figures 5A, 5B, 5C:
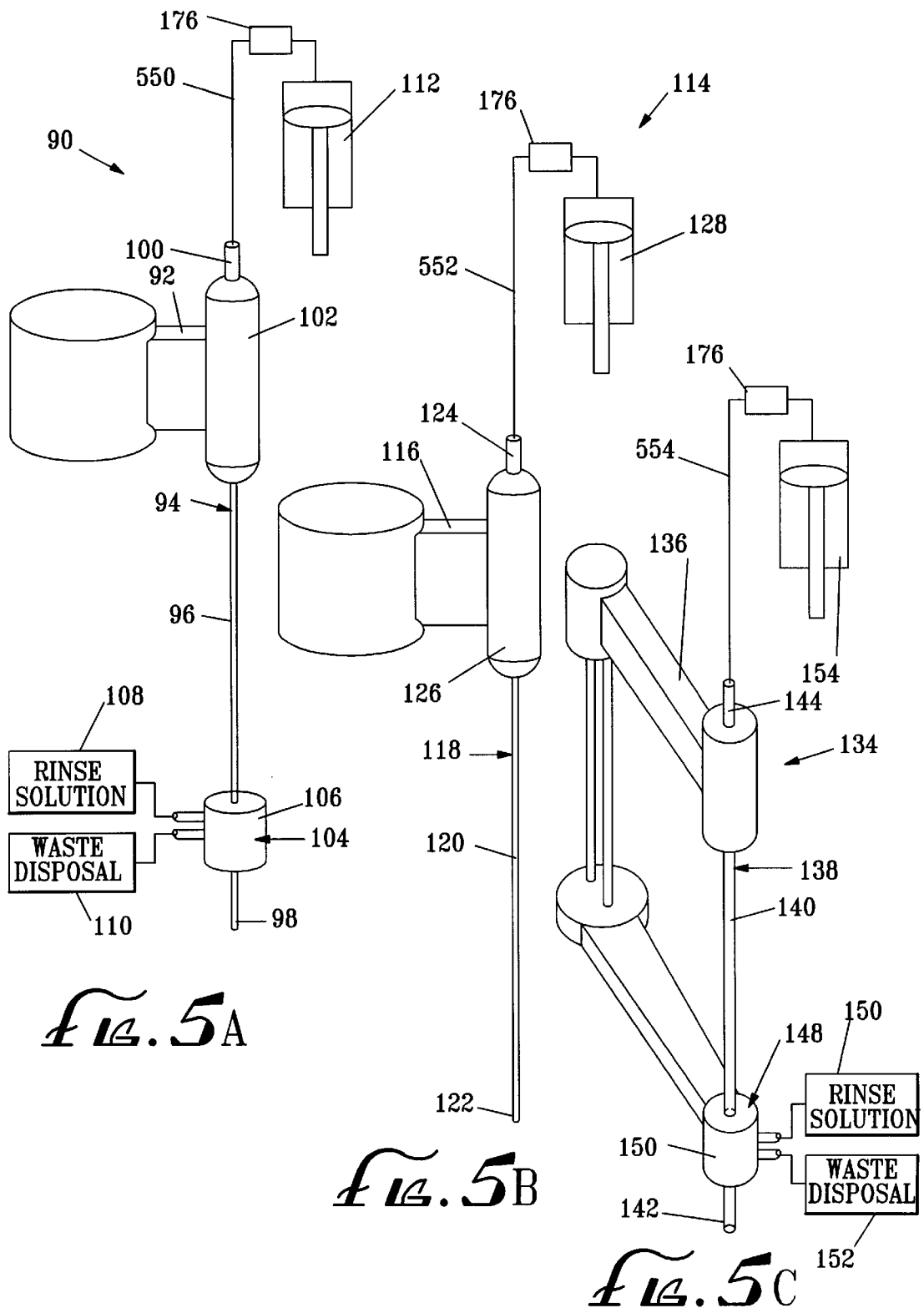
FIG. 5A is a perspective view of a sample probe arm assemble useful in the invention.
FIG. 5B is a perspective view of a reagent probe arm assembly.
FIG. 5C is a perspective view of a cup analyze probe arm assembly.

The analyzing machine 10 further comprises a motorized sample probe arm assembly 90 such as shown in FIG. 5A. The sample probe arm assembly 90 includes a sample probe arm 92 and a hollow sample probe 94. The sample probe 94 has an internal chamber 96, an open lower end 98 and an open upper end 100. The sample probe 94 is disposed generally vertically in the sample probe arm 92 and is movable by a sample probe motor 102 between a lower sample probe position and an upper sample probe position.

The sample probe 94 can be equipped with a sample probe tip cleaning assembly 104 such as is described in U.S. Pat. No. 5,408,891, the entirety of which is incorporated herein by this reference. Such cleaning assembly 104 includes a cleaning assembly chamber 106 connected in fluid tight communication with a source of cleaning liquid 108 and a disposal site 110.

The sample probe arm 92 is movable by a sample probe arm motor (not shown) between a first sample probe arm position wherein the sample probe is immediately above the sample extraction site 38 and a second sample probe arm position wherein the sample probe is immediately above the cuvette sample deposit site 50.

The sample probe 94 is connected to sample probe pressure altering means capable of alternatively applying a positive pressure and a negative pressure to the internal chamber 96 of the sample probe 94. Such pressure altering means can be any of the various pressure altering means known in the art. Typically, such pressure altering means is provided by a syringe pump 112.

The sample probe arm assembly 90 is used to extract a predetermined quantity of sample from a sample container 32 disposed within the sample station 14 at the sample extraction site 38 and transport that quantity of sample to a cuvette 44 disposed within the random access analyzing station 18 at the cuvette sample deposit site 50.

The analyzing machine 10 further comprises a motorized reagent probe arm assembly 114 such as shown in FIG. 5B. The reagent probe arm assembly 114 includes a reagent probe arm 116 and a hollow reagent probe 118. The reagent probe 118 has an internal chamber 120, an open lower end 122 and an open upper end 124. The reagent probe 118 is disposed generally vertically in the reagent probe arm 116 and is movable by a reagent probe motor 126 between a lower reagent probe position and an upper reagent probe position.

The reagent probe arm 116 is movable by a reagent probe arm motor (not shown) between a first reagent probe arm position wherein the reagent probe 118 is immediately above the reagent extraction site 42 and a second reagent probe arm position wherein the reagent probe is immediately above the cuvette reagent deposit site 52.

The reagent probe 118 is connected to reagent probe pressure altering means capable of alternatively applying a positive pressure and a negative pressure to the internal chamber 120 of the reagent probe 118. Such pressure altering means can be any of the various pressure altering means known in the art. Typically, such pressure altering means is provided by a syringe pump 128.

The reagent probe arm 116 is used to extract a predetermined quantity of reagent from a reagent container 40 disposed within the reagent station 16 at the reagent extraction site 42 and transporting that quantity of reagent to a cuvette 44 disposed within the random access analyzing station 18 at the cuvette reagent deposit site 52.

Both the sample probe arm 92 and the reagent probe arm 116 can include multiple independently movable probes. In the embodiment illustrated in the drawings, both the sample probe arm 92 and the reagent probe arm 116 comprise a pair of probes each independently movable about a primary axis of rotation 130. Both probe arms are also rotatable as a whole about a secondary axis of rotation 132.

The analyzing machine 110 further comprises a cup analysis probe arm assembly 134 such as shown in FIG. 5C. The cup analysis probe arm assembly 134 includes a cup analysis probe arm 136 and a hollow cup analysis probe 138. The cup analysis probe 138 has an internal chamber 140, a lower end 142 and an open upper end 144. The cup analysis probe 138 is disposed generally vertically in the cup analysis probe arm 136 and is movable by a cup analysis probe motor (not shown) between a lower cup analysis probe position and an upper analysis probe position.

The cup analysis probe 138 can be equipped with a cup analysis probe tip cleaning assembly 146 such as is known in the prior art. Such cleaning assembly includes a cleaning assembly chamber 148 connected in fluid tight communication with a source of cleaning liquid 150 and a disposal site 152.

The cup analysis probe arm 136 is movable by a cup analysis probe arm motor (not shown) between a first cup analysis probe arm position wherein the cup analysis probe is immediately above a sample container 32 in the sample station 14, a second cup analysis probe arm position wherein the cup analysis probe 136 is immediately above one of the reaction cup modules 58 and a third cup analysis probe arm position wherein the cup analysis probe 136 is immediately above the sample injection cup 60.

The cup analysis probe 136 is connected to cup analysis probe pressure altering means capable of alternatively applying a positive pressure and a negative pressure to the internal chamber 140 of the cup analysis probe 136. Such pressure altering means can be any of the various pressure latering means known in the art. Typically, such pressure altering means is provided by a syringe pump 154.

The cup analysis probe arm assembly 134 is used to extract a predetermined quantity of sample from a sample container 32 disposed within the sample station 14 and transport that quantity to each of the reaction cup modules 58 and to the sample injection cup 60.

The analyzing machine 10 further comprises a cuvette stirring rod assembly 156 such as shown in FIG. 5D. The cuvette stirring rod arm assembly 156 includes an elongate rotatable cuvette stirring rod 158 having a lower end 160 and an upper end 162. The lower end 160 of the cuvette stirring rod includes a cuvette stirring rod paddle 164 attached thereto. The cuvette stirring rod is generally disposed vertically and is movable between a lower cuvette stirring rod position and an upper stirring rod position. The cuvette stirring rod arm assembly 156 is positionable above the cuvette mixing site 54. As illustrated by the embodiments shown in the drawings, the motorized cuvette stirring rod assembly 156 can be an independent and separate assembly or it can be integrated with the sample probe arm 92 and/or the reagent probe arm 116.

The analyzing machine 10 further comprises a cuvette wash station 166 as shown in FIG. 5E. The cuvette wash station probe 168 is used to extract liquid reaction mixtures from the cuvettes 44, dispose such mixtures to a suitable disposal site and then rinse and clean the cuvette 44 so that it can be used to analyze another quantity of sample.

The wash station 166 comprises one or more motorized cuvette wash station probes 168. Each wash station probe 168 has an internal chamber 170, an open lower end 172 and an open upper end 174. The wash station probe 168 is disposed generally vertically above the cuvette washing site 56 in the random access analyzing station 18 and is movable by a wash station probe motor (not shown) between a lower wash station probe position and an upper wash station probe position.

In the embodiment shown in the drawings, the wash station probes 168 operated in pairs, one of each pair of wash station probes 168 being connected to a source of pressurized rinse solution and the other wash station probe 168 of each pair being connected to a disposal system adapted to vacuum out the contents of a cuvette and transfer such contents to a suitable disposal site.

Alternatively, each individual wash station probe 168 can be connected to the wash station probe pressure altering means capable of alternatively applying a positive pressure and a negative pressure to the internal chamber 170 of the wash station probe 168. The wash station probe pressure altering means includes means for providing pressurized washing liquid from a source of washing liquid to the wash station probe 168 for washing a cuvette disposed at the cuvette washing site 56 and means for providing a negative pressure to the interior chamber 170 of the wash station probe 168 for removing waste liquids from a cuvette disposed at the cuvette washing site 56 and for transferring such waste liquids to a disposal site. Such means for providing negative pressure to the interior chamber 170 typically comprises a source of vacuum.

Each of the pressure altering means usable in the analyzing machine can further comprise an obstruction detector 176 comprising a pressure transducer operatively installed within the operative pressure transmitting conduits to alert the operator and/or shut down the machine should an obstructive pressure drop be detected within the pressure altering means. Such an obstruction detector 176 is described in detail in U.S. patent application Ser. No. 08/748,135, entitled AUTOMATIC CHEMISTRY ANALYZER WITH OBSTRUCTION DETECTION SYSTEM (presently pending), filed contemporaneously herewith, and which is incorporated herein in its entirety.

Typically, the automated analyzing machine 10 further comprises a controller 178 for controlling each of the various motors in a way which provides for the smooth, efficient and rapid operation of the machine 10. The control is typically also used to retain and report analysis data. Preferably, the controller 178 comprises a digital computer which can be preprogrammed with a large variety of operating instructions depending upon the samples being analyzed, the analyses to be run and the reagents at hand. Most preferably, the digital computer receives bar coded information regarding each of the samples to be analyzed, and the reagents in the reagent station 16 and uses that information to most efficiently conduct the analyses. Also, it is preferable that the controller 178 keep track of the amounts of reagents used so as to alert the operator whenever reagent in any particular reagent container 40 begins to run low.

Also, it is preferable that the controller 178 include a "stat" mode, which gives the operator the ability to require the machine 10 to analyze particularly important samples in the reaction cup and ion selective electrode analyzing stations ahead of all other samples.

Figure 6:
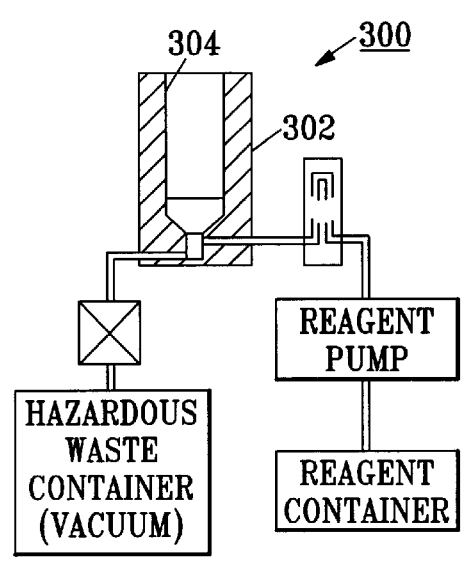
FIG. 6 is a flow diagram showing a reaction cup combination known in the prior art.

FIG. 6 is a flow diagram for a typical prior art reaction cup module. FIG. 7 illustrates the structure of such a typical reaction cup module. FIGS. 8–13B illustrate the improved reaction cup module 58 of the invention.

As illustrated in FIG. 6, in a typical analysis operation, reagent is pumped into a reaction cup from a source of reagent (typically stored within the body) via a reagent pump. A sample is then deposited in the reaction cup, usually via some sort of sample extraction probe. The sample and reagent mixture within the reaction cup is agitated using, for example, a magnetically driven impeller disposed at the base of the cup. The reaction mixture is then analyzed by one of several different analyzing techniques depending upon the chemistry employed and the analysis mixture is then drained to a disposal site. The reaction cup is then rinsed one or more times to remove substantially all traces of the prior reaction mixture. The rinse liquid is also drained to a disposal site leaving the reaction cup clean and empty and ready for a new sample.

Generally, reactions within the reaction cup are carried out at a precisely controlled elevated temperature such as 37° C. To accomplish this, the reagent rinsing liquid and/or the reaction cup are heated with a heating element.

As illustrated in FIG. 7, a typical reaction cup module 300 of the prior art includes a cylindrical body 302, a reaction cup 304 disposed within the body 302, a stirring impeller 306 driven by a rotating magnet 308 and an analyzer 310. Reagent is used for both the analysis chemistry conducted within the reaction cup 304 and for rinsing the reaction cup 304 clean between analyses. Reagent is brought into the reaction cup 304 via an inlet line 312 which is wrapped repeatedly around the cylindrical body 302. The inlet line 312 typically requires at least two layers, a first layer 314 in abutment with the body and a second layer 316 in abutment with the first layer 314.

The body 302 and the inlet line 312 are heated with a heating element 318 disposed between the body 302 and the first inlet line layer 314. Temperature control is typically attempted by measuring the temperature of the reaction cup wall 320.

There are several problems with this prior art design. The multiple layers of inlet line 312 diminish the efficiency of heat transfer between the heating element 318 and the reagent within the inlet line 312. This results in low throughput because the reagent must be heated to the elevated reaction cup temperature. Also, it has been found that temperature control using a measurement of the reaction cup wall 320 is often less than wholly precise.

Figure 8:
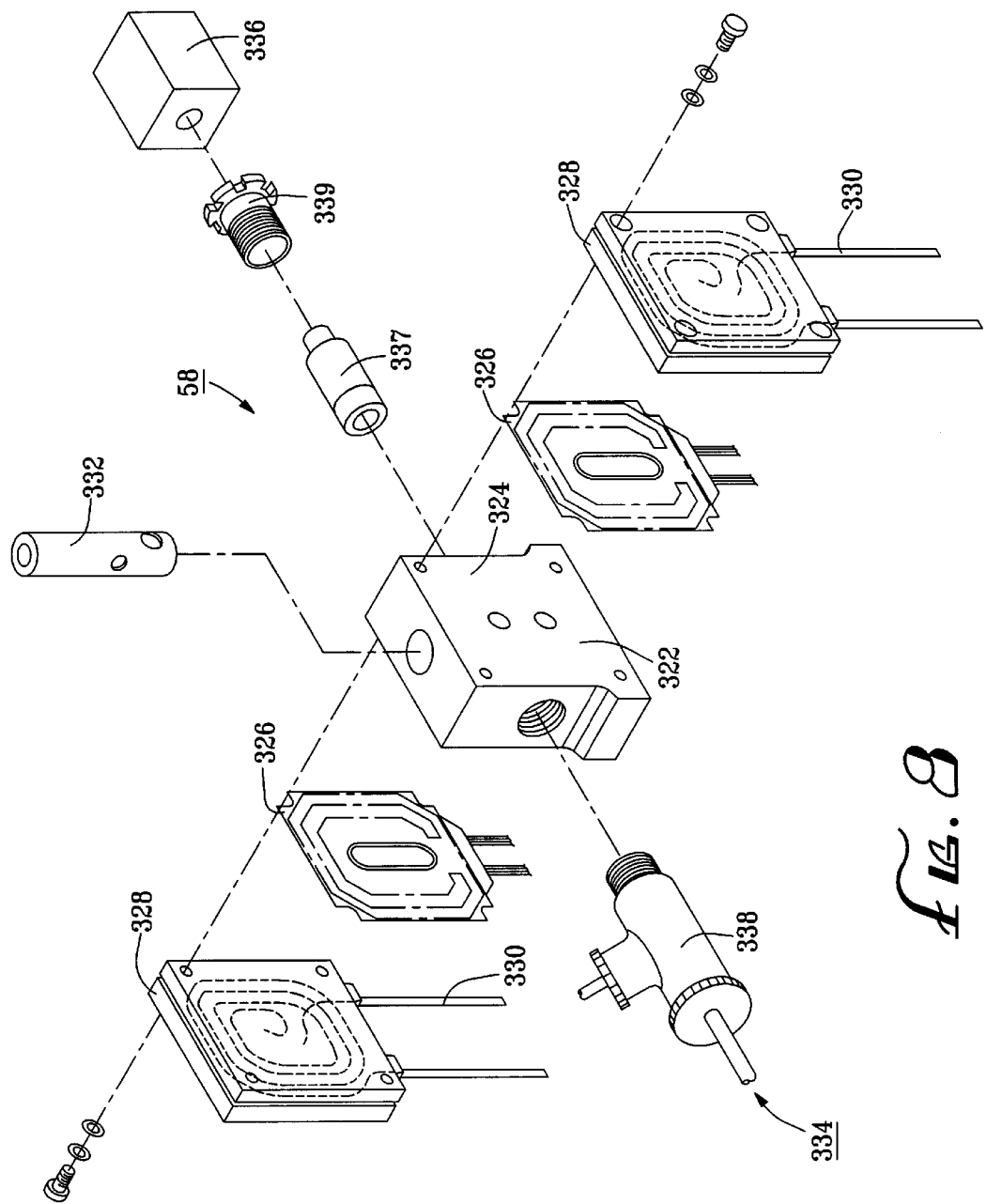
FIG. 8 is an exploded perspective view of a reaction cup assembly having features of the invention.

Contrasted with the reaction cup module of the prior art is the reaction cup module 58 of the invention as illustrated in FIG. 8. The reaction cup module 58 of the invention comprises a body 322 which is preferably made from a solid block of a metal or other material having a high heat transfer coefficient. For ease of manufacture, aluminum is a preferred material for the body 322. The body has a pair of opposed substantially smooth flat sides 324. In abutment with each flat side 324 is a planar heating element 326. Sandwiching each planar heating element 326 against a flat side 324 of the body 322 is a planar side wall 328. Within the planar side wall 328, separate inlet conduits 330 are disposed in coiled or similar fashion so as to be disposed in a single plane. By this design, substantially the entire length of the inlet conduit 330 within the module 58 is in abutment with the heating element 326. Unlike the design of the prior art, there are no multiple layers of inlet conduit 330. This design, therefore, markedly increases the efficient in the heating of liquids flowing into a reaction cup 332 disposed within the body 322.

As further illustrated in FIG. 8, the reaction cup module 58 of the invention also comprises an analyzer 334. The analyzer 334 can be a nephelometric analyzer comprising a light source 336, a light pipe 337 and a light receptor 338. The light receptor 338 is attached to the body 322 so that the light receptor 338 is in abutment with a transparent portion of the reaction cup 332. Opposite the light receptor 338, the light pipe 337 is disposed within the body 322 in abutment with a second transparent portion of the reaction cup 332, such that the light pipe 337 and the light receptor 338 are in alignment through the transparent portions of the reaction cup 332. In the embodiment shown in FIG. 8, the light pipe 337 is held fast within the body 322 by a light pipe retainer 339. The light source 336 is aligned with the light receptor 338 and the light pipe 337. The light source 336 is physically attached to the body 322 by suitable attachment structure (not shown). Preferably, such attachment structure minimizes heat transfer from the light source 336 to the body 322. Such an attachment structure minimizes problems in maintaining heat control within the reaction cup 332.

In alternative embodiments, the analyzer 334 can be an electrode, usually specifically designed to measure for a particular analyte.

The reaction cup module 58 of the invention can also comprise a magnetic stirrer (not shown).

Figure 9:
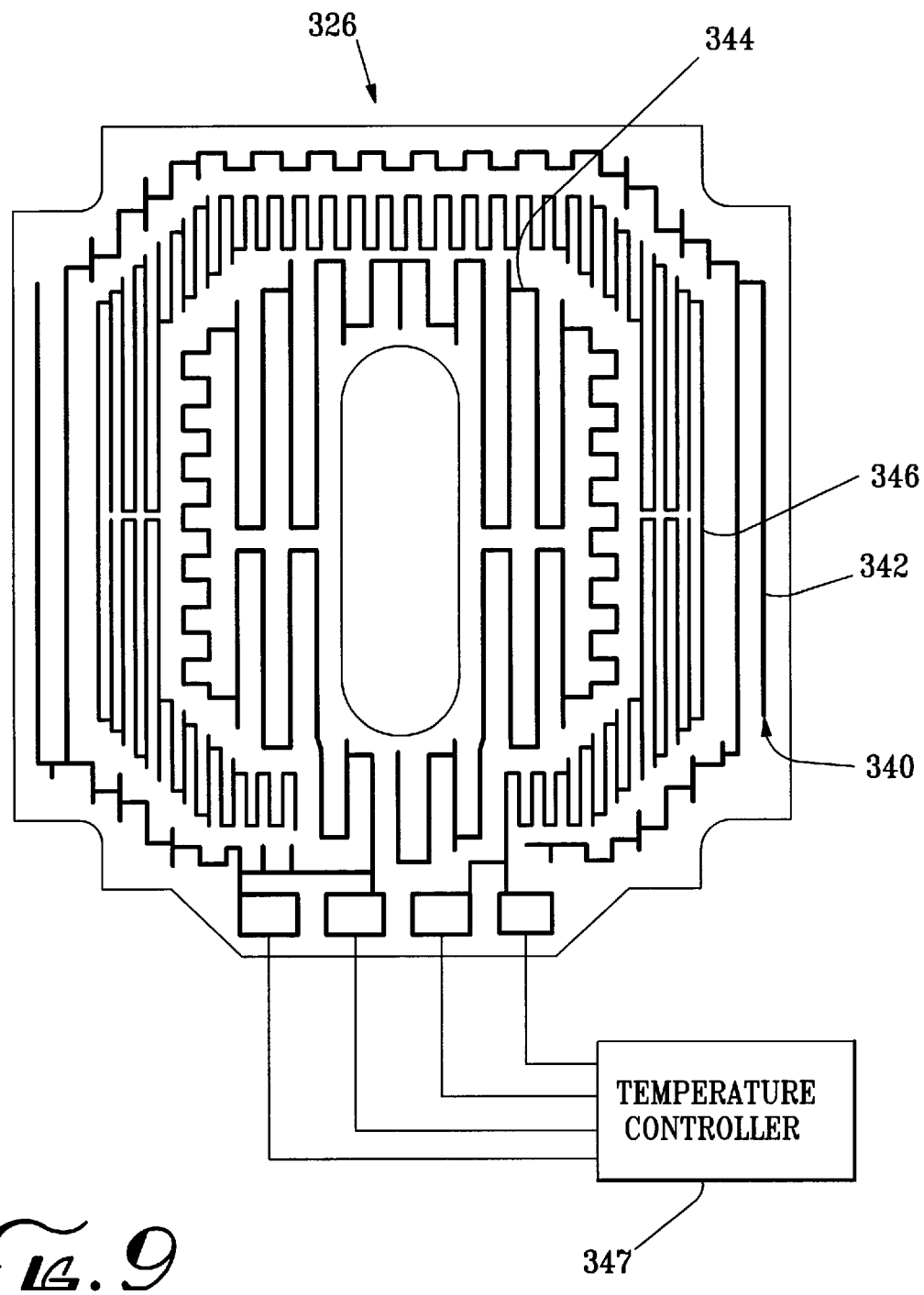
FIG. 9 is a plan view of a heating element useful in the invention.

FIG. 9 illustrates a typical heating element 326 useful in the invention.

The heating element 326 is disposed on a flat surface in a planar pattern 340. As shown in FIG. 9 it is preferable that the planar pattern 340 include an outside heating element moiety 342 and an inside heating element moiety 344. This preferred pattern 340 allows a temperature sensor 346 to be disposed between the outside moiety 342 and the inside moiety 344. Such disposition provides for a high degree of precision in the control of the temperature of the reaction cup 332. Temperature control is maintained by monitoring the temperature of the inlet conduit 330 by sensing the temperature of the inlet conduit 330 with the temperature sensor 346 (which is disposed in abutment with the temperature inlet conduit 330) and by controlling the operation of the heating element 342 (to maintain a predetermined temperature in the inlet conduit 330) using temperature controller 347. Controlling the temperature within the reaction cup 332 by controlling the temperature of the incoming fluids within the inlet conduit 330 has been found to be preferable to attempting to monitor the temperature of the reaction cup 332, itself (the method generally used in prior art devices, such as illustrated in FIG. 7).

Typically, the heating element 326 is capable of transferring between about 10 and about 40 BTU's of heat.

As shown in FIG. 6, the only liquid available for rinsing the reaction cup 304 in the prior art is the expensive and sometimes toxic reagent used in the chemistry conducted within the reaction cup 304.

Figure 10:
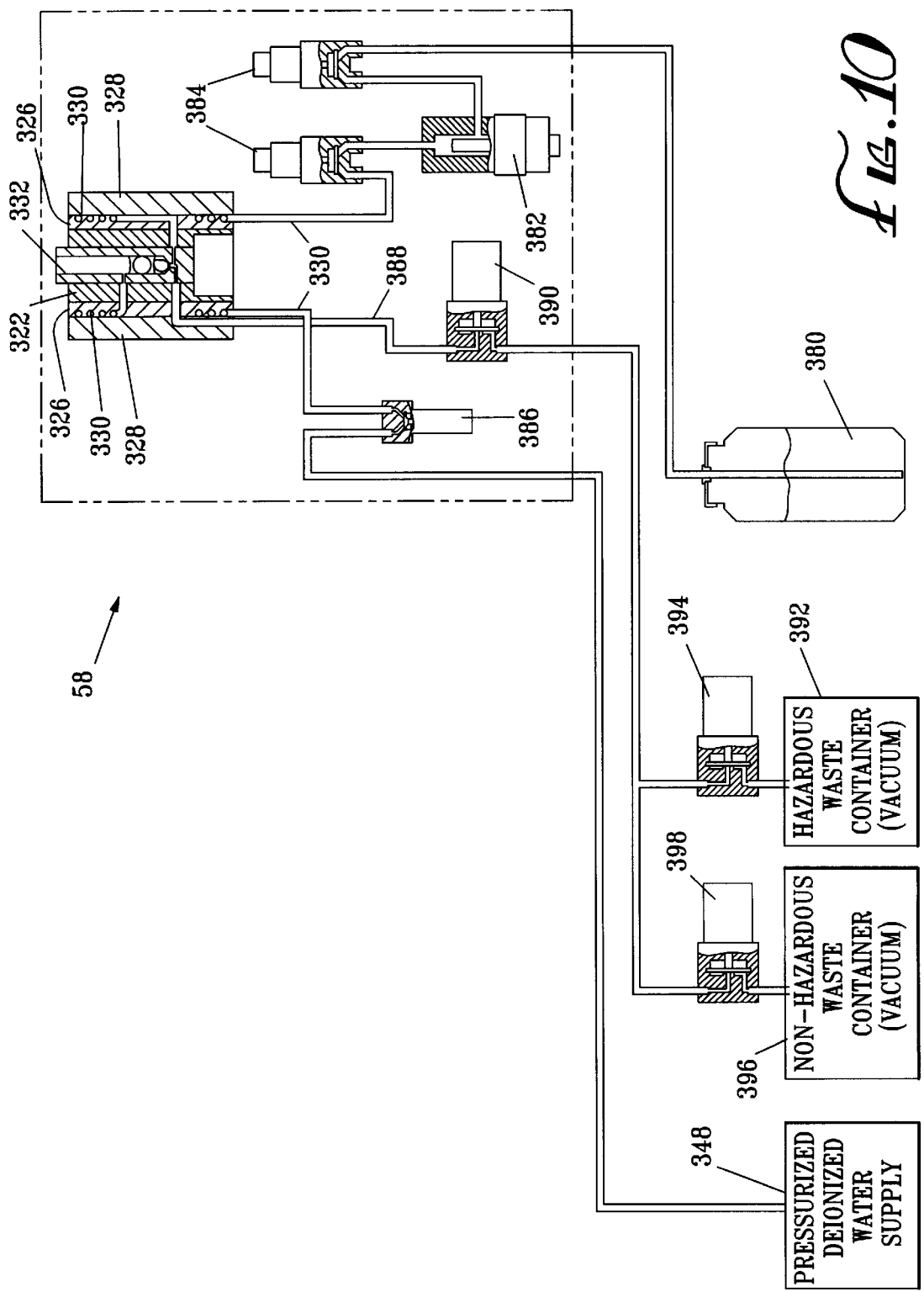
FIG. 10 is a flow diagram showing a reaction cup combination having features of the invention.

Contrasted with the flow scheme of the prior art is the flow scheme preferred in the invention as illustrated in FIG. 10. Reagent is provided to the reaction cup 332 via an inlet conduit on one side of the reaction cup module 58 (the right side on FIG. 10). Reagent is pumped from a source of reagent 380 by a reagent pump 382 through remote controllable reagent valves 384 into the inlet conduit 330. Within that portion of the inlet conduit 330 which is partially disposed within the reaction cup module 58, reagent is heated by heating element 326 before flowing into the reaction cup 332. Deionized rinse water is provided to the reaction cup 332 from a pressurized source of deionized water 348 through a remote controllable deionized water valve 386 and into the inlet conduit 330 on the side of the reaction cup module 58 opposite the inlet conduit 330 through which reagent flows into the reaction cup 332. In that portion of the inlet conduit 330 which is disposed within the reaction cup module 58, deionized rinse water is heated by heating element 326 immediately prior to its flow into the reaction cup 332.

The reaction cup 332 is drained via a drain line 388 through a remote controllable master drain valve 390. When the liquid to be drained is of a potentially hazardous sort, the liquid is drained to a suitable hazardous waste container 392 through a remote controllable hazardous waste container valve 394. Where the liquid to be drained is of a non-hazardous sort, the liquid is drained to a suitable non-hazardous waste container 396 through a remote controllable non-hazardous waste container valve 398. Both the hazardous and non-hazardous waste containers 392 and 396 are typically maintained under vacuum to facilitate rapid and complete draining of liquid from the reaction cup 332. Because a separate deionized rinse water source 348 is provided to the reaction cup 332, such deionized rinse water is conveniently and inexpensively used in the rinsing step.

Moreover, because water is used in the rinse steps, much of the liquid drained from the reaction cup during the rinsing step can be disposed in a non-hazardous waste disposal area. Note further that because two separate heating elements 326 are used, time lags required for heating are much reduced. This is especially true in analysis operations requiring multiple rinse cycles.

The use of the rinse water system also provides another substantial benefit over the prior art. The analyzing machine 10 using the cup analysis module 58 of the invention can be programmed to periodically and automatically recalibrate a nephelometer used as an analyzer 334, by briefly filling the reaction 332 cup with pure rinse water and calibrating the nephelometer to a predetermined set point. This eliminates having to periodically shut down the machine 10 and manually calibrating each of the nephelometers used in the various reaction cup modules 58.

Figure 11:
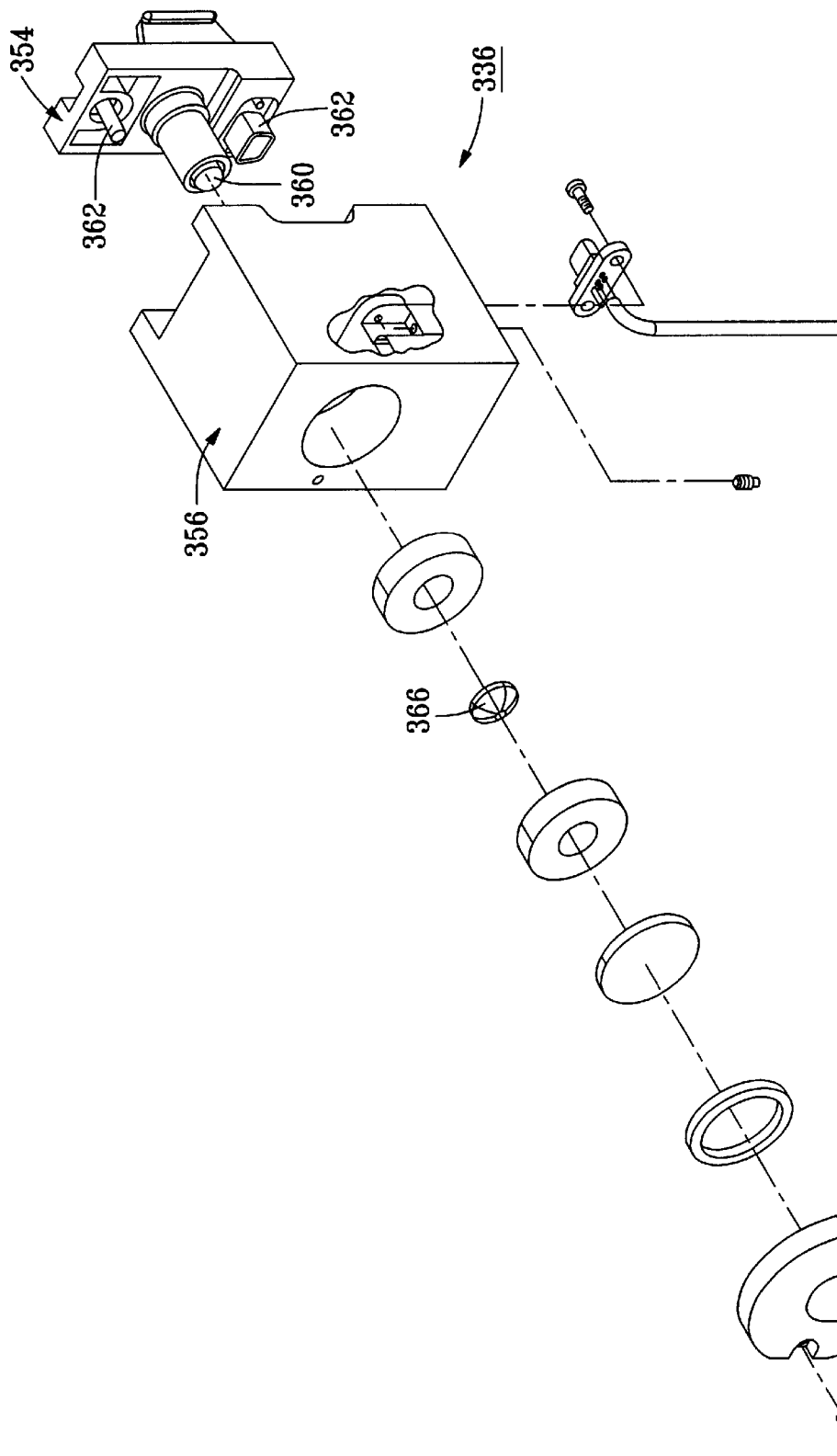
FIG. 11 is an exploded perspective view of a light source housing having features of the invention.

FIG. 11 illustrates an improved nephelometer light source 336 useful in the invention. This improved nephelometer includes a bulb housing moiety 354 and a lens housing moiety 356.

As shown in FIGS. 12A, 12B and 12C, the bulb housing moiety 354 rigidly receives and retains a light source bulb 360. The light source bulb can be an incondecent bulb or it can be a light emitting diode ("LED"). The bulb housing moiety 354 has male connection elements 362 which are snugly received within corresponding female connector elements 364 in the lens housing moiety 356. A light source lens 366 is held rigidly within the lens housing moiety 356. By this design, the light source bulb 360 is maintained in alignment with the light source lens 366. Thus, when and if the light source bulb 360 burns out, no expensive alignment of the light source 336 is required. The user merely replaces the bulb housing moiety 354 and reinstalls the bulb housing moiety 354 into the lens housing moiety 356. Because of the rigid and precise construction of the two moieties, realignment of the new light source bulb 360 and the existing light source lens 366 is assured.

Also, the invention allows the operator to run the light source 366 with minimum power. In the prior art, power was usually maximized to allow calibration with shutters disposed forward of the light source lens 366. Without the need for such shutters, the light source can be operated at lower power. This significantly increases light source bulb life.

FIGS. 13A and 13B illustrates the light receptor housing 358 of the invention. The light receptor housing 358 comprises a light inlet moiety 400 and a light receptor moiety 370. The light receptor moiety 370 houses a light receptor lens in rigid alignment with a light receptor (not shown). The light receptor monitors the quantity of incident light received into the light receptor housing 358 and transmits an appropriate control signal via other suitable transmission equipment 406. Various filters (not shown) can be interposed along the light path so that the light receptor monitors the quantity of incident light within a narrow wave length band only.

As shown in FIG. 13A, the nephelometer can be "biochromatic," comprising a pair of light receptor moieties 370 and adapted to measure light at two different frequencies. A beam splitter 381 directs a portion of the light entering the light receptor moiety 370', and directs the remainder to a second light receptor moiety 370". Such a biochromatic assembly can be used to analyze samples with one light receptor moiety 370 (by measuring incident light of one frequency), while simultaneously monitoring assembly calibration with the other light receptor moiety 370 (by measuring incident light of another frequency).

In the light receptor housing 358 of the invention, the light inlet moiety 400 is rigidly affixed in alignment with the light receptor moiety 370 by means of a rigid threaded connection 408. By this rigid construction, problems of alignment between the incident light within the light receptor housing 358 and the light receptor are minimized. The rigid construction of the light receptor housing 358 of the invention is contrasted with the light receptor housing 372 of the prior art as illustrated in FIG. 14. In the light receptor housing 372 of the prior art, the light inlet moiety 410 is attached to the light receptor moiety 412 using a bayonet connection which depends for rigidity on an O-ring 378. As can be easily recognized by one of skill in the art, this connection is much less rigid than the connection used in the light receptor housing 358 of the invention. Consequently, the light receptor housing 372 of the prior art is susceptible to misalignments between the incident light within the light receptor housing 372 and the light receptor disposed within the light receptor moiety 412. Even casual contact with the light receptor moiety 412 can cause the light receptor to become misaligned with respect to incident light within the light receptor housing 372. Thus, the user of prior art machines can only be sure that its nephelometer is properly calibrated by frequently shutting down the machine and calibrating the nephelometer. This is unduly time-consuming and expensive. For this reason, the light receptor housing 358 of the invention provides a significant improvement over the light receptor housing 372 of the prior art.

The light receptor housing 358 can be made even more rigid by incorporation of an anti-rotational tab 379 as shown in FIG. 13B. The anti-rotational tab 379 is typically a laterally extending prong rigidly attached to the side of the light receptor housing 358. The anti-rotational tab 379 is used to prevent rotation of the light receptor housing 358 with respect to the body 322 of the reaction cup module 58 by slipping into and thereby cooperating with a corresponding groove (not shown) defined within the wall of the body 322.

The reaction cup module 58 can be used with a single rinse cycle or with a double rinse cycle, such as for high creatinine sample analyses.

An automated analyzing machine 10 having a reaction cup module 58 of the invention can typically test a sample simultaneously for creatinine, total protein, albumin, inorganic phosphorous, BUN and glucose. Repeated samples can be simultaneously analyzed for one or more of the above parameters in a turn-around time of less than about 45 seconds per sample, preferably about 40 seconds per sample.

Moreover, when an automated analyzing machine 10 having the reaction cup module 58 of the invention further comprises an ion selective electrode analyzing station 22 described herein, the machine 10 can typically simultaneously analyze for the concentration of creatinine, total protein, albumin, inorganic phosphorous, BUN, glucose, sodium, potassium, calcium, chlorine and carbon dioxide in a series of liquid samples with a throughput time of less than about 45 seconds per sample, preferably about 40 seconds per sample. This represents a considerable improvement over the prior art and represents a significant increase in profitability to the user.

In operation, the operator of the automated analyzing machine of the invention 10 places samples to be analyzed in individual sample containers 32 and places each sample container 32 in one or more sample container racks 34. The sample container racks 34 are placed in the on-load tray 76.

The motorized loading arm 80 pushes sample container racks 34 in the on-load tray 76 towards the loading mechanism path 74. As each sample container rack 34 enters the loading mechanism path 74, the motorized loading path arm 82 pushes the sample container rack 34 along the loading mechanism path 74 towards the sample station 14.

As the sample containers 32 pass by the bar code reader 84, bar-coded information appended to each sample container 32 is read by the bar code reader 84 and is transmitted to the controller 178. Such bar code coded information typically includes the identity of the sample and the analyses which are to be run using individual portions of the sample.

As the sample container rack 34 is pushed further along the loading mechanism path 74, it passes under the cap piercing mechanism 86. The cap piercing mechanism 86 pierces the caps 36 on each of the sample containers 32.

The sample container rack 34 then is loaded into the sample station 14 wherein a clamping means within the sample station 14 holds the sample container rack 34 firmly upright.

The sample station 14 is rotated under the control of the controller 178.

When an individual sample container 32 is placed at a sample extraction site 38, a small quantity of the sample is extracted from the sample container 32 by the sample probe 94. This is accomplished by positioning the sample probe 94 above the sample extraction site 38, lowering the sample probe 94 to the lower sample probe position wherein the open-ended lower end 98 of the sample probe 94 is placed below the surface of the sample within the sample container 32. A small quantity of the sample is then extracted into the sample probe internal chamber 96 by drawing a vacuum on the sample probe internal chamber 96 using the sample probe pressure altering means. The sample probe 94 is then raised to the upper sample probe position and the sample probe arm 92 moves the sample probe 94 to a position where it is directly above the cuvette sample deposit site 50.

At the cuvette sample deposit site 50, the sample probe 94 is again lowered to the lower sample probe position and the quantity of sample within the sample probe 94 is deposited into a cuvette 44 positioned at the cuvette sample deposit site 50. This is done by creating a slight elevated pressure within the sample probe internal chamber 96 using the sample probe pressure altering means. The lower end of the sample probe 94 is then retracted into the sample probe tip cleaning assembly 104 where it is rinsed using cleaning liquid from the source of cleaning liquid 108. After cleaning, the cleaning liquid is flushed to a suitable disposal site 110. The sample probe 94 is then ready to extract another quantity of sample from another sample container 32.

Contemporaneously with the above-described action of the sample probe 94, the reagent probe 118 is used in similar fashion to extract a quantity of an appropriate pre-mixed reagent from the reagent station 16 and depositing that quantity of reagent into the cuvette 44. Usually the reagent is added to the cuvette immediately prior to the deposit of the sample within the cuvette 44.

After sample and reagent are both added to the cuvette 44, the cuvette 44 is rotated to the cuvette mixing site 54. At the cuvette mixing site 54, the cuvette stirring rod 158 is lowered to the lower cuvette stirring rod position and the stirring rod paddle 164 is rotated so as to agitate and thoroughly mix the sample and reagent within the cuvette 44.

In typical random access analyzing operations wherein analyses are carried out at an elevated temperature, the mixture of sample and reagent within the cuvette 44 is then allowed to stand within the random access analyzing station 18 while the mixture is brought up to temperature, such as by blowing heated air through the random access analyzing station 18. When the mixture within the cuvette 44 has reached proper temperature, the contents of the cuvette 44 are analyzed using the random access analyzing station analyzer 46. In a preferred operation, the cuvette 44 is placed at the random access analyzing station analyzing site 46 a plurality of times and is thereby analyzed a plurality of times so that the reportable results are derived from an average of the plurality of analyses. The reportable results are thereby extremely reliable.

After analyses are completed regarding the mixture within the cuvette 44, the cuvette 44 is moved to the cuvette washing site 56 at the cuvette wash station 166. At the cuvette wash station 166, a wash station probe 168 is moved from its upper probe position to the lower probe position and the reaction mixture is extracted using the wash station pressure altering means. Depending upon the kind of mixture which had been analyzed within the cuvette 44, the cuvette 44 is then rinsed once or several times using pressurized washing liquid. After the rinse liquid is removed from the cuvette 44 and sent to suitable disposal, the cuvette 44 is ready to accept another sample for analysis.

Contemporaneously with the operation of the random access analyzing station 18, high volume analyses are performed in the reaction cup analyzing station 20 and in the ion selective electrode analyzing station 22. First, a predetermined quantity of an appropriate reagent is pumped into each reaction cup 332 and into the injection sample cup 60 using the reagent pump 59. The magnetic stirrer is engaged. Then, the cup analysis probe arm assembly 134 positions the cup analysis probe 136 above a sample container 32 within the sample station 14, the cup analysis probe 136 is lowered to the lower probe position and a relatively large quantity of sample is extracted into the internal chamber 140 within the cup analysis probe 138 using the cup analysis probe pressure altering means. The cup analysis probe 138 is then raised to the upper probe position and the cup analysis probe arm 136 moves the cup analysis probe 138 to a position directly above one of the reaction cup modules 58. The cup analysis probe 138 is lowered to the lower cup position and a portion of the sample within the cup analysis probe 138 is deposited within the reaction cup 332. The cup analysis probe 138 is then again raised to the upper probe position and the cup analysis probe arm 136 moves the cup analysis probe 138 to immediately above each of the other reaction cup modules 58 and deposits a portion of the sample within each such reaction cups 332.

When all of the reaction cups 332 are filled, the cup analysis probe arm 136 moves the cup analysis probe 138 to directly above the sample injection cup 60. The cup analysis probe 138 is again lowered to the lower probe position and the remainder of the sample is deposited within the injection sample cup 60.

After the mixture of reagent and sample is thoroughly mixed by the magnetic stirrer, the mixture is analyzed using the reaction cup analyzing station analyzer 334 in each cup module, and the results of the analyses are reported to the controller 178. The reaction cups 332 are then rinsed and ready for another sample.

Contemporaneously, in the ion specific electrode analysis station, the quantity of sample within the injection sample cup 60 is thoroughly flow mixed with the reagent. After the sample and reagent are properly mixed, the mixture is passed through the flow cell 62 where individual electrodes within the flow cell 62 each perform a single analysis on the mixture. The results of the analysis are reported to the controller 178. The mixture is then drained to a suitable disposal site 66 and the system is rinsed in preparation for the analysis of another sample.

After the sample within each of the sample containers 32 in a sample container rack 34 are analyzed, the sample container rack 34 is removed from the sample station 14 using the motorized loading path arm 82. The sample container rack 34 is retracted along the loading mechanism path 74 to the off-load tray 78. Once in the off-load tray 78, the motorized unloading arm pushes the sample container rack 34 towards the end of the off-load tray 78 where it is removed by the operator.

The invention provides significant improvements over the prior art by reducing throughput times, maintenance costs and operating expense, while increasing accuracy and reliability.

Although the present invention has been described in considerable detail with reference to certain preferred versions thereof, other versions are possible. Therefore, the spirit and scope of the appended claims should not be limited to the description of the preferred versions contained herein.

What is claimed is:

1. A reaction cup combination useful for automated chemical analyses comprising:
    (a) a body having at least one substantially smooth flat side;
    (b) a reaction cup disposed within the body;
    (c) an analyzer for analyzing liquids disposed within the reaction cup;
    (d) a planar heating element disposed in abutment with the flat side of the body;
    (e) a planar side wall disposed proximate to the heating element;
    (f) an inlet conduit comprising an inlet conduit wall, the inlet conduit being disposed in fluid communication with the reaction cup and disposed substantially within the planar side wall such that the inlet conduit is in abutment with the heating element;
    (g) a temperature sensor for sensing the temperature of the inlet conduit wall; and
    (h) a temperature controller operatively connected to the temperature sensor and to the heating element for controlling the temperature of fluids within the inlet conduit.

2. The reaction cup combination of claim 1 wherein the body is made from a metal.

3. The reaction cup combination of claim 1 wherein the body is made from aluminum.

4. The reaction cup combination of claim 1 wherein the body has a first substantially flat side and a second substantially flat side and wherein the reaction cup combination comprises;
    (a) a first planar heating element disposed in abutment with the first flat side of the body;
    (b) a first planar side wall disposed proximate to the first heating element;
    (c) a first inlet conduit disposed in fluid communication with the reaction cup, the first inlet conduit being disposed substantially within the first planar side wall such that the first inlet conduit is in abutment with the first heating element;
    (d) a second planar heating element disposed in abutment with the second flat side of the body;

(e) a second planar side wall disposed proximate to the second heating element; and (f) a second inlet conduit disposed in fluid communication with the reaction cup, the second inlet conduit being disposed substantially within the second planar side wall such that the second inlet conduit is in abutment with the second heating element.

5. The reaction cup combination of claim 1 wherein the reaction cup combination comprises;

(a) a first drain conduit disposed in fluid communication with the reaction cup, the first drain conduit comprising a first drain conduit valve disposed therein;

(b) a second drain conduit disposed in fluid communication with the reaction cup, the second drain conduit comprising a second drain conduit valve disposed therein; and (c) a drain valve controller for controlling the opening and closing of the first and second drain conduit valves.

6. The reaction cup combination of claim 1 wherein the heating element is capable of transferring between about 10 and about 40 BTU of heat.

7. The reaction cup combination of claim 1 further comprising a temperature sensor disposed in abutment with the inlet conduit wall.

8. The reaction cup combination of claim 7 wherein the heating element is disposed in a planar pattern having an outside moiety and an inside moiety and wherein the temperature sensor is disposed within a planar pattern located between the outside moiety of the heating element and the inside moiety of the heating element.

9. The reaction cup combination of claim 1 wherein the analyzer comprises an electrode.

10. The reaction cup combination of claim 1 wherein the analyzer comprises a light source and a light sensor.

11. The reaction cup combination of claim 1 wherein the reaction cup has side walls with opposed first and second substantially transparent wall portions and wherein the reaction cup combination further comprises:

(a) a light source housing disposed adjacent to the first transparent wall portion, the light source housing including a bulb housing moiety and a lens housing moiety;

(b) a light receptor housing disposed adjacent to the second transparent wall portion;

(c) a light receptor disposed within the light receptor housing;

(d) a light bulb rigidly affixed within the bulb housing moiety so that light produced by the light bulb is directed into the lens housing moiety; and (e) a lens rigidly affixed within the lens housing moiety so that light produced by the light bulb is directed through the first and second transparent wall portions to the light receptor, the lens being separate and spaced apart from the light bulb.

12. The reaction cup combination of claim 1 wherein the reaction cup has side walls with opposed first and second substantially transparent wall portions and wherein the reaction cup combination further comprises:

(a) a reaction cup having side walls with opposed first and second substantially transparent wall portions;

(b) a light source housing disposed adjacent to the first transparent wall portion;

(c) a light receptor housing rigidly disposed adjacent to the second transparent wall portion;

(d) a light bulb and lens affixed within the light source housing so that light produced by the light bulb is directed by the lens through the first and second transparent wall portions to the light receptor housing; and (e) a light receptor rigidly disposed within the light receptor housing.

13. A device for determining at least one parameter of a liquid sample, the device comprising:

(a) a body;

(b) a sample station disposed within the body, the sample station being sized and dimensioned to retain a plurality of sample containers;

(c) a reagent station disposed within the body, the reagent station being sized and dimensioned to retain a plurality of reagent containers;

(d) a reaction cup analyzing station disposed within the body, the reaction cup analyzing station comprising:

(i) a body having at least one substantially smooth flat side;

(ii) a reaction cup disposed within the body;

(iii) an analyzer for analyzing liquids disposed within the reaction cup;

(iv) a planar heating element disposed in abutment with the flat side of the body;

(v) a planar side wall disposed proximate to the heating element;

(vi) an inlet conduit comprising an inlet conduit wall, the inlet conduit being disposed in fluid communication with the reaction cup and disposed substantially within the planar side wall such that the inlet conduit is in abutment with the heating element;

(vii) a temperature sensor for sensing the temperature of the inlet conduit wall; and (viii) a temperature controller operatively connected to the temperature sensor and to the heating element for controlling the temperature of fluids within the inlet conduit;

(e) an ion selective electrode analyzing station disposed within the body, the ion selective analyzing station comprising: (1) a sample injection cup in fluid tight communication with a flow cell analyzer for measuring at least one electrolyte in a liquid sample and (2) ion selective electrode analyzing station pump means for pumping ion selective electrode analyzing station reagent from a source of ion selective electrode analyzing station reagent to the sample injection cup and for pumping the contents of the sample reaction cup through the flow cell analyzer and then to a suitable disposal site; and (f) sample transfer means for transferring liquid sample from a sample container to the reaction cup and to the sample injection cup.

14. The device of claim 13 wherein the reaction cup has side walls with opposed first and second substantially transparent wall portions and wherein the reaction cup combination further comprises:

(a) a light source housing disposed adjacent to the first transparent wall portion, the light source housing including a bulb housing moiety and a lens housing moiety;

(b) a light receptor housing disposed adjacent to the second transparent wall portion;

(c) a light receptor disposed within the light receptor housing;

(d) a light bulb rigidly affixed within the bulb housing moiety so that light produced by the light bulb is directed into the lens housing moiety; and (e) a lens rigidly affixed within the lens housing moiety so that light produced by the light bulb is directed through the first and second transparent wall portions to the light receptor, the lens being separate and spaced apart from the light bulb.

15. The device of claim 13 wherein the reaction cup has side walls with opposed first and second substantially transparent wall portions and wherein the reaction cup combination further comprises:

(a) a reaction cup having side walls with opposed first and second substantially transparent wall portions;

(b) a light source housing disposed adjacent to the first transparent wall portion;

(c) a light receptor housing rigidly disposed adjacent to the second transparent wall portion;

(d) a light bulb and lens affixed within the light source housing so that light produced by the light bulb is directed by the lens through the first and second transparent wall portions to the light receptor housing; and (e) a light receptor rigidly disposed within the light receptor housing.

16. The device of claim 13 herein the sample transfer means comprises:

(a) a cup analysis probe arm assembly attached to the body, the cup analysis probe arm assembly including (1) a motorized cup analysis probe arm and (2) a motorized, hollow cup analysis probe having an internal chamber, an open lower end and an open upper end, the cup analysis probe being vertically movable between a lower cup analysis probe position and an upper cup analysis probe position, the cup analysis probe arm being movable between a first cup analysis probe arm position wherein the cup analysis probe is immediately above a sample container, a second cup analysis probe arm position wherein the cup analysis probe is immediately above the reaction cup and a third cup analysis probe arm position wherein the cup analysis probe is immediately above the injection sample cup; and (b) cup analysis probe pressure altering means for alternatively applying a positive pressure and a negative pressure to the interior chamber of the cup analysis probe.

\* \* \* \* \*